(12) United States Patent
Knott et al.

(10) Patent No.: US 8,576,191 B2
(45) Date of Patent: Nov. 5, 2013

(54) DISPLAY AND CONTROL DEVICE FOR MEDICAL EQUIPMENT

(75) Inventors: Erwin Knott, Poing (DE); Ottmar Penka, München (DE); Andreas Hahn, Berg (DE)

(73) Assignee: Sorin Group Deutschland GmbH, München (DE)

( * ) Notice: Subject to any disclaimer, the term of this patent is extended or adjusted under 35 U.S.C. 154(b) by 25 days.

(21) Appl. No.: 13/158,822

(22) Filed: Jun. 13, 2011

(65) Prior Publication Data

US 2011/0254794 A1 Oct. 20, 2011

Related U.S. Application Data

(63) Continuation of application No. 10/566,330, filed as application No. PCT/EP2004/008499 on Jul. 29, 2004, now Pat. No. 7,961,156.

(30) Foreign Application Priority Data

Jul. 29, 2003 (DE) .................................. 103 34 516

(51) Int. Cl.
*G09G 5/00* (2006.01)

(52) U.S. Cl.
USPC ............. 345/173; 345/1.1; 600/508; 600/529

(58) Field of Classification Search
USPC .................. 345/1.1, 4, 30, 173; 600/508–545
See application file for complete search history.

(56) References Cited

U.S. PATENT DOCUMENTS

| | | | | |
|---|---|---|---|---|
| 4,800,376 A | * | 1/1989 | Suga et al. ...................... | 345/1.3 |
| 5,111,103 A | * | 5/1992 | DuBrucq ........................ | 313/2.1 |
| 5,561,412 A | * | 10/1996 | Novak et al. ............. | 340/286.07 |
| 5,591,344 A | | 1/1997 | Kenley et al. | |
| 5,699,038 A | * | 12/1997 | Ulrich et al. ............. | 340/286.07 |
| 5,752,931 A | | 5/1998 | Nazarian et al. | |
| 5,788,851 A | | 8/1998 | Kenley et al. | |
| 5,838,223 A | * | 11/1998 | Gallant et al. ........... | 340/286.07 |

(Continued)

FOREIGN PATENT DOCUMENTS

| | | |
|---|---|---|
| DE | 10013666 A1 | 10/2001 |
| DE | 10334516 B4 | 3/2005 |

(Continued)

OTHER PUBLICATIONS

European Search Report issued in EP Application No. 12175890, dated Dec. 18, 2012, 10 pages.

(Continued)

*Primary Examiner* — Amare Mengistu
*Assistant Examiner* — Vinh Lam
(74) *Attorney, Agent, or Firm* — Faegre Baker Daniels LLP

(57) ABSTRACT

A display and control device for medical equipment, comprising several identically configured display/control units, which are located on a base unit. The base unit is equipped with a bus, to which the display/control units and components of the medical equipment are connected. The base unit comprises connection devices, which are used to connect the display/control units to the bus. Once a display/control unit has been connected, a configuration unit transmits configuration data to the display/control unit and only then defines which function the display/control unit is to fulfill. This permits defective display/control units to be simply replaced. The construction of the display/control units is likewise simple and not susceptible to malfunctions.

17 Claims, 6 Drawing Sheets

(56) References Cited

U.S. PATENT DOCUMENTS

| | | | |
|---|---|---|---|
| 6,143,181 A * | 11/2000 | Falkvall et al. ............... 210/646 |
| 6,496,359 B2 | 12/2002 | Clark et al. |
| 6,681,764 B1 * | 1/2004 | Honkonen et al. ....... 128/201.21 |
| 6,738,052 B1 * | 5/2004 | Manke et al. ................. 345/177 |
| 7,961,156 B2 | 6/2011 | Knott et al. |
| 2003/0052787 A1 * | 3/2003 | Zerhusen et al. .......... 340/573.1 |
| 2003/0067437 A1 | 4/2003 | McClintock et al. |
| 2003/0179156 A1 * | 9/2003 | Willmore ....................... 345/1.1 |
| 2007/0052683 A1 | 3/2007 | Knott et al. |
| 2011/0254794 A1 | 10/2011 | Knott et al. |

FOREIGN PATENT DOCUMENTS

| | | | |
|---|---|---|---|
| EP | 0114713 B1 | 8/1984 |
| EP | 1202162 A1 | 5/2002 |
| EP | 1246052 A1 | 10/2002 |
| JP | 62163478 A | 7/1987 |
| JP | 888820 A | 4/1996 |
| JP | 11262522 A | 9/1999 |
| JP | 2000504988 A | 4/2000 |
| JP | 2002196741 A | 7/2002 |
| WO | WO0008531 A1 | 2/2000 |
| WO | WO0220348 A2 | 4/2002 |

OTHER PUBLICATIONS

International Preliminary Report on Patentability issued in PCT/EP2004/008499, mailed Feb. 4, 2005, with English translation, 20 pages.

International Search Report issued in PCT/EP2004/008499, mailed Feb. 4, 2005, 4 pages.

* cited by examiner

DISPLAY AND CONTROL DEVICE FOR MEDICAL EQUIPMENT

CROSS-REFERENCE TO RELATED APPLICATION

This application is a continuation of U.S. patent application Ser. No. 10/566,330, filed Sep. 11, 2006, entitled "Display and Control Device for Medical Equipment," which is a national phase application of PCT/EP2004/008499 (now WO2005/013113), filed Jul. 29, 2004, which claims priority to German patent application 10334516.7 filed Jul. 29, 2003, each of which are herein incorporated by reference in their entirety.

TECHNICAL FIELD

The present invention relates to a display and control device for medical equipment, in particular life support systems such as heart-lung machines or artificial respiration devices .

BACKGROUND

In order to be able to safely operate and monitor medical equipment, display and control devices must be provided on this equipment, which allow the user to determine the operating state of the equipment in a clear manner and to intervene in the operation of the equipment using control elements. Thus, in heart-lung machines, for example, (hereinafter also referred to as HLM) display and control elements are provided for the different units and components, e.g. the blood pumps or the oxygenator, via which the user can monitor and influence the operation of the HLM units. In addition, display and control elements are provided for various sensors, for example fill level sensors, temperature sensors or air bubble detectors, on which the user can read a measured value of a sensor and set limiting values which trigger an alarm or other action if they are exceeded or gone below. In HLM, these display and control elements have recently often been combined in the form of a display and control panel so that the user can clearly monitor and control the operation of the entire heart-lung machine at one position.

SUMMARY

Display and control panels of the type discussed herein are increasingly being realized using program-controlled screens and keypad units. Recently, these user interfaces (GUI=Graphical User Interface) have been used in the form of LCD displays in combination with a touch-sensitive cover of the LCD display surface (touch screen). This means that the user can not only read values on the display but can also operate buttons, switches and regulators depicted on the display by touching the display surface in the area where a button, switch or regulator is depicted.

The use of such touch-screen GUI units allows simple operation of even complex systems, in particular by reducing the control elements and thereby increasing clarity, by means of a context-dependent design of the control possibilities and by means of situation-dependent support by the system. GUI units of this type also offer advantages with regard to production, in particular in high quantities. However, it is disadvantageous that when using a GUI unit, a display defect can lead to a complete loss of system control. Interaction with the user via the GUI unit is no longer possible in the case of a total failure. Even partial failures can lead to an unacceptable impairment of the operability of the medical device. It must be noted in this regard that touch-sensitive surfaces are by nature susceptible to mechanical defects. In addition, a complex and expensive development process for the GUI unit and its controls is necessary for complex applications, in particular when realizing language-specific variants.

As a result, such display and control devices can only be used for safety-critical applications in life support systems such as heart-lung machines or artificial respiration devices at substantial cost (redundant control panels, specifically adapted operating systems, etc). Where a redundant design is not possible or expedient, the display and control device must be provided as an exchangeable part which, upon failure of the display and control device being used, can be exchanged therewith. This procedure is, however, unsatisfactory in view of the costs for providing a replacement panel.

In view of the above, the aim of the invention is to specify a display and control device for medical equipment, in particular heart-lung machines or other life support systems such as artificial respiration systems, in which continued operation can be ensured in an economic manner in the case of a defect.

This aim is achieved by a display and control device having the features of patent claim 1. Advantageous embodiments can be seen from the sub-claims.

According to the invention, a plurality of touch-screen GUI units are combined into one modular display and control device. The GUI units are virtually identical in structure and are designed as plug-in modules which can be attached at various positions of a base panel. Setting of the display and control function of the individual touch-screen GUI unit is effected by a configuration device, with which the touch-screen GUI unit is connected via a bus system (in the base) and from which it receives configuration data. The configuration data determine, via the display contents and input areas, the display and control function of the touch-screen GUI unit.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

In the following, the invention will be explained in more detail by means of an embodiment with reference to the figures, in which.

Figure 1:
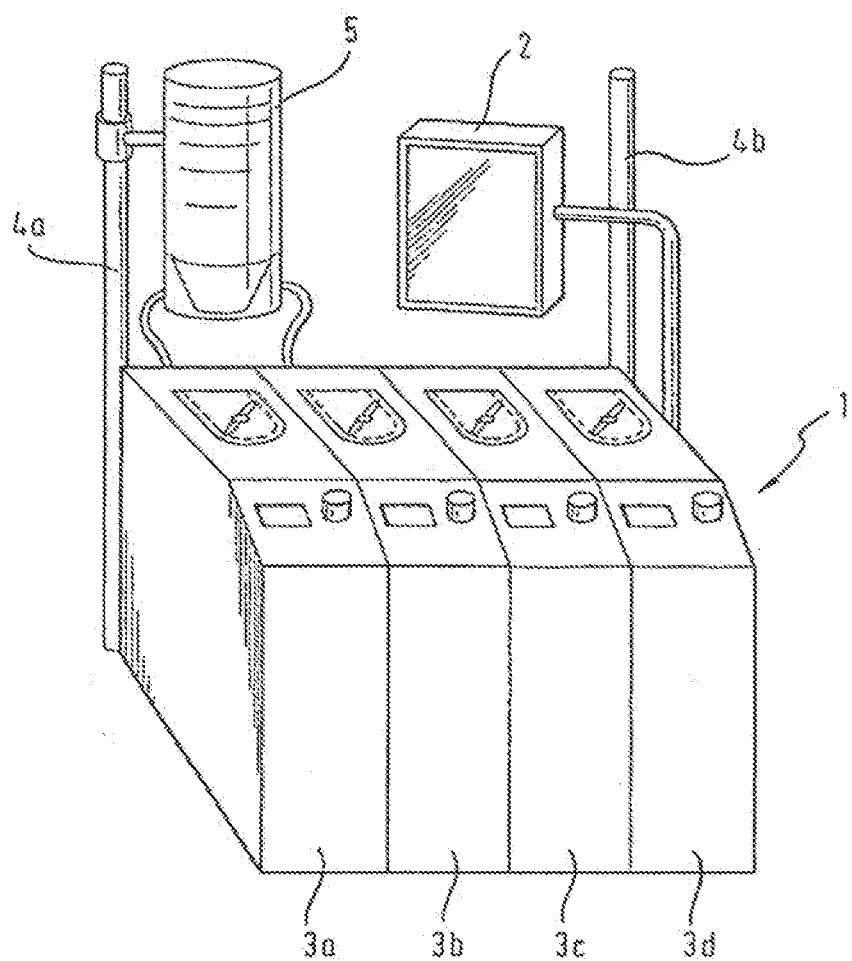
FIG. 1 schematically shows the structure of an HLM as an example of a life support system in particular and a medical device in general that is particularly suitable for explaining the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 schematically shows a heart-lung machine 1, which is used as an example to explain a display and control device 2 as can be found in medical equipment, in particular in life support systems such as heart-lung machines and respiration systems.

The heart-lung machine 1 shown in FIG. 1 comprises four blood pumps 3a, 3b, 3c and 3d which are disposed one next to the other. The casings of the blood pumps form the body of the HLM 1. Further aggregates or units of the HLM 1 can be arranged on fixing masts 4a and 4b, such as, for example, the schematically indicated blood reservoir 5. In addition, sensors (not shown) are normally present in an HLM to detect various measured values such as temperatures, pressures and flows. Furthermore, bubble detectors (not shown) are normally provided, by means of which it can be ensured that blood containing air bubbles is not supplied to the patient. There is no intention here of listing in full all the units or components of an HLM. The aforementioned units are mentioned merely as examples on the basis of an HLM but also for the other life support systems and medical equipment. However, an HLM as well as artificial respiration devices are particularly suitable for the use of the invention.

The display and control device 2 discussed above, by means of which the units or components of the HLM 1 can be monitored or controlled, is provided on the HLM 1 shown in FIG. 1. For this purpose, the display and control device 2 shows various values, some of which are measured values of the sensors and detectors and some of which are operating parameters of the units, such as, for example, the rotational speed of the blood pumps, or other values, e.g. times. The display of the values gives the user an overview of the operating status of the HLM 1 and via the display and control device 2, the user can intervene for control by using the control elements depicted in the display and control device.

Figure 2:
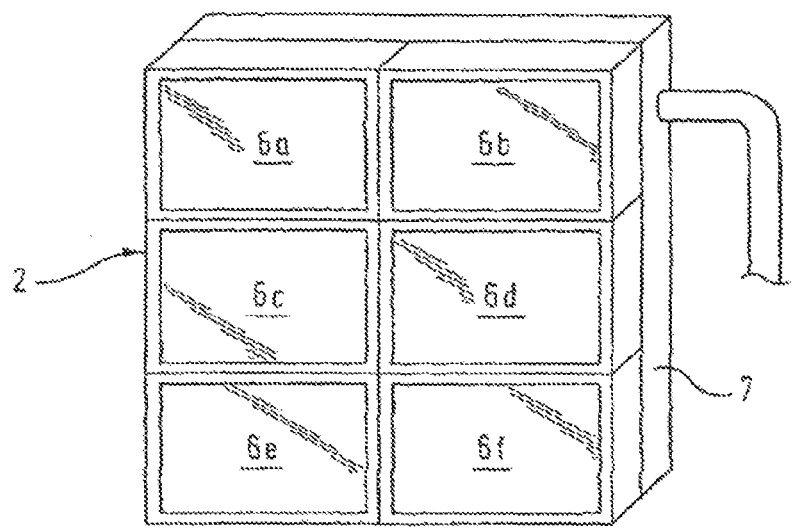
FIG. 2 shows a perspective view of the structure of a display and control device according to the invention.
Figure 3:
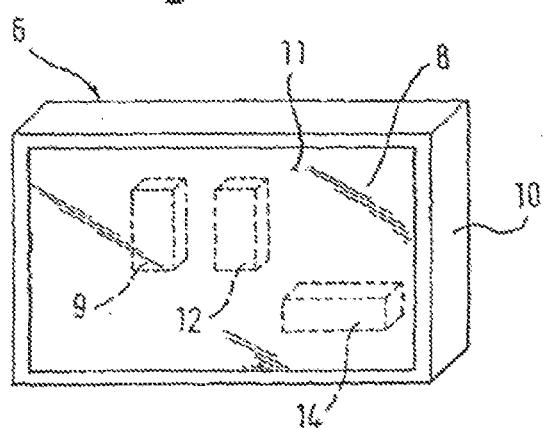
FIG. 3. shows a perspective view of the front of a display/control unit according to the invention.

FIG. 2 shows a display and control device 2 according to the invention; this device comprises a plurality of display/control units 6a to 6f, which are arranged on a base unit 7. As can be seen from FIG. 3, which shows a front view of a display/control unit 6 according to the invention, each display/control unit 6 comprises a flat display device 8 that has a plurality of activatable pixels and on which both measured values in the form of numerical values as well as text or graphic elements can be displayed. For this purpose, the display/control unit 6 is equipped with a display activation device 9, which activates the pixels of the display device 8 on the basis of data supplied. The display activation device 9 is preferably provided in a housing 10 of the display/control unit 6, which is why it is shown with dashed lines in the view seen in FIG. 3. To create an input possibility, each display/control unit has a transparent input device 11, which is disposed on the surface of the display device 8 facing the observer and which is connected with an input evaluation device 12 that evaluates the inputs made via the input device 11. The input evaluation device 12 is preferably also accommodated in the housing 10 and is therefore shown with dashed lines. Overall, a touch-screen display/input unit 6 is created in this manner, which can on the one hand display information (8, 9) and on the other receive inputs (11, 12). Further display or control elements are not necessary according to the invention but may, however, be provided. In particular, an on/off switch may be provided so that the display/control unit 6 is not active when the display/control unit 6 is mounted on the base unit 7.

Figure 4:
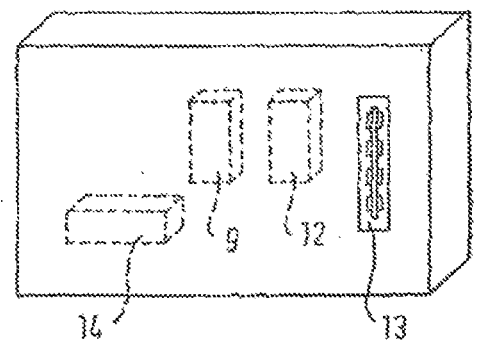
FIG. 4. shows a perspective view of the rear of a display/control unit according to the invention.

So that the data for the display contents can be transmitted to the display activation device 9 and the inputs can be passed on by the input evaluation device 12, the display/control unit 6 has a connection means 13, which is shown in FIG. 4—a rear view of a display/control unit. The display activation device 9 and the input evaluation device 12 are connected with the connection means 13 so that the display/control unit 6 according to the invention can be connected to an electric bus.

The electric bus addressed here is a connection system which allows electric devices connected to the bus to communicate with other devices connected to the bus. This basically means that values or other information can be transmitted, i.e. sent and received, in a targeted manner from one bus device to another.

Depending on the type of bus used, a bus communication device 14 can be expediently provided, which on the one hand guarantees the connection to the bus and on the other is connected with the display activation device 9 and the input evaluation device 12, whereby the display activation device 9 and the input evaluation device 12 do not need to be designed for direct connection to the bus.

Figure 5:
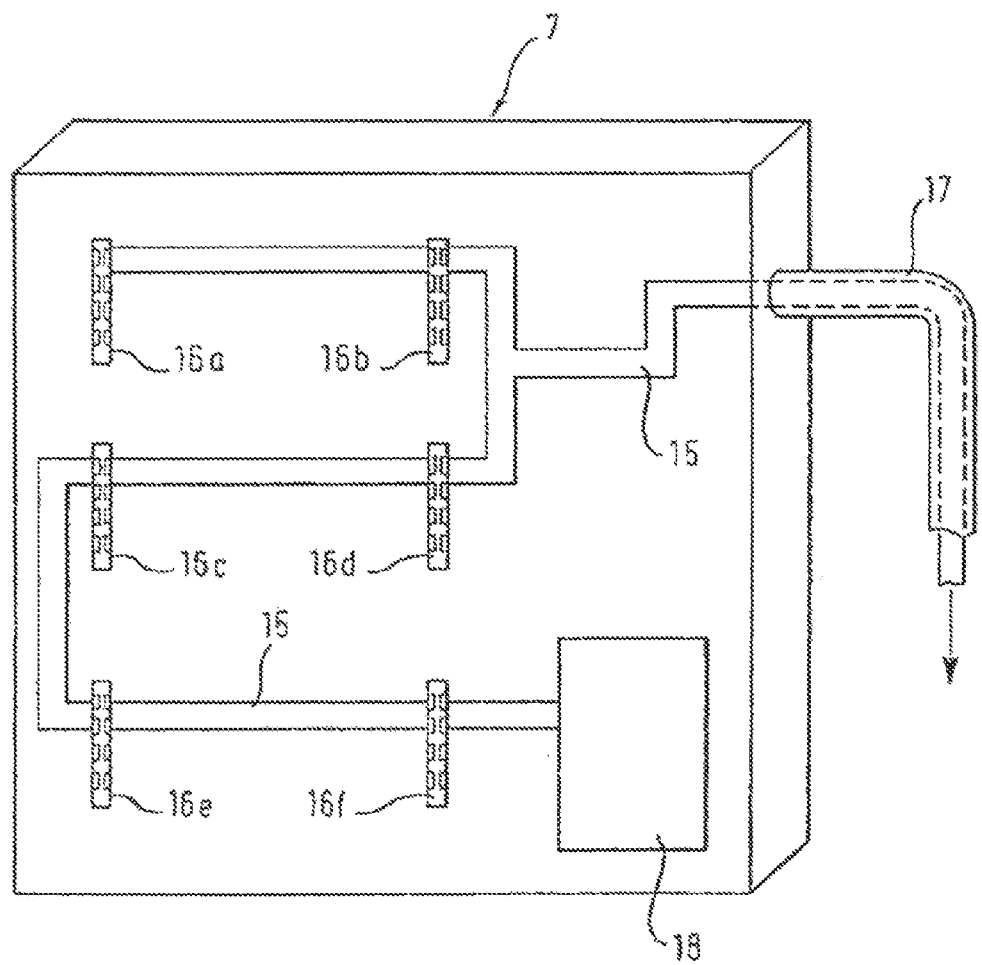
FIG. 5. shows a perspective view of the structure of a base unit according to the invention.

As FIG. 5 shows, the bus 15 is provided in the base unit 7 of the display and control device 2 according to the invention.

As already stated, it assists communication of units connected to the bus. So that the display/control units 6a to 6f can be connected to the bus, suitable connector devices 16a to 16f are provided on the base unit 7. Each connector device 16 in the base unit 7 is adapted to the connection means 13 of the display/control unit 6 so that by bringing together a connection means 13 and a connector device 16, preferably according to the plug and socket principle, a display/control unit 6 can be connected to the bus 15 when the display/control unit 6 is disposed on the base unit 7.

The connection between the connector device 16 and the connection means 13 is either such that a sufficient mechanical fixing of the display/control unit 6 to the base unit 7 is achieved or such that additional provisions for mechanical fixing have to be made, which will, however, not be described in more detail here. In principle, any fixing of the display/control unit 6 to the base unit 7 which can easily be created and detached by a user is suitable, however the requirements existing in the field of medical equipment and in particular life support systems must be observed.

The bus 15 is guided out of the base unit 7, as shown in FIG. 5, for example through the support 17 of the display and control device 2. The bus is guided into the medical equipment via the support 17, as can be seen, for example, in the HLM in FIG. 1 so that the units and aggregates of the medical equipment can also be connected to the bus.

A configuration unit 18, which is also connected with the electric bus 15, is furthermore provided in the base unit 7. Immediately after connection of a display/control unit 6 to the bus, i.e. usually when the display/control unit 6 is attached to the base unit 7, the configuration unit 18 assumes the function of transmitting initial data to the display/control unit 6. These data are configuration data that inform the display/control unit 6 of the task which it must assume within the entirety of the display and control device 2. Configuration of the display/control unit 6 is an important aspect of the display and control device 2 according to the invention since a display/control unit 6 can be used in different manners as a result thereof because it is only the configuration data that determine the purpose for which the display/control unit 6 is used. The configuration data transmitted via the electric bus 15 are essentially information (instructions) which establishes the display contents and input areas of the display/control unit 6. The display activation device 9 of the display/control unit 6 must show the display contents transmitted by the configuration data on the display 8 of the display/control unit 6 (FIG. 3); the input evaluation device 12 must accordingly evaluate the sections on the surface 11 of the display 8 defined by the configuration data as input areas and monitor these for inputs by the user.

Since the display/control units 6 of a display and control device 2 according to the invention are constructed in a virtually identical manner, each display/control unit 6 can be used at any position (16a to 16f) of the base unit 7. This means that during use of the medical equipment, for example the HLM in the operating theatre, only one display/control unit generally need be kept available as a replacement part since should any display/control unit in the display and control device fail, the redundant display/control unit can be used as a replacement. In addition, a display/control unit that is already being used can be taken out of operation if its function is of secondary importance (e.g. time display) and can be used in place of a failed display/control unit which supports critical monitoring and control functions that are essential for the user.

In addition to the possibility of keeping one display/control unit available as an inexpensive replacement part, the invention also creates the possibility of ensuring secure operation owing to the redundant design of the configuration device 18. The redundant design of the configuration device 18 is an acceptable expenditure which makes the invention possible. In addition, it must be noted that during operation of the display and control device according to the invention, the configuration device 18 does not assume any other functions. This means that once configuration of the display/control units has been completed, the failure of the configuration device during operation does not initially constitute a deterioration in the overall function of the display and control device according to the invention. However, a fault in the configuration device 18 should be signaled to the user since if the configuration device 18 is faulty, it is no longer possible to exchange a display/control unit 6.

In the following, it will be described as an example in which form configuration data are transmitted from the configuration device 18 to a display/control unit 6 and how the configuration data are processed in the display/control unit 6.

Figure 6:
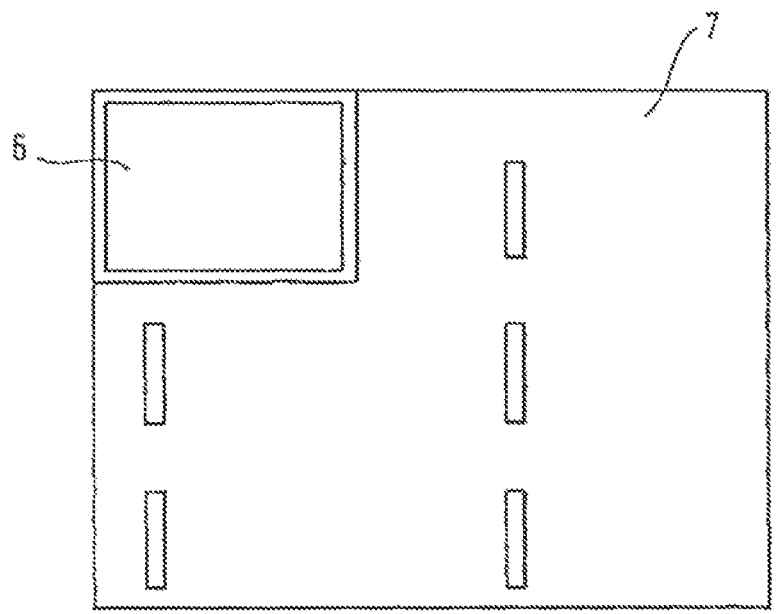
FIG. 6. shows a view of a base unit and display/control unit according to the invention which is disposed thereon.

For this purpose, FIG. 6 shows a base unit 7 to which a display/control unit 6 is attached. When a display/control unit 6 is disposed on the base unit 7 and is connected to the electric bus 15 in the base unit 7 by bringing together the connection means 13 and the connector device 16, it is signaled to the configuration device 18 via the bus 15 that and to which connector device 16a to 16f a display/control unit 6 has been attached. Since the position of the connector device 16a in the embodiment described here determines which display contents are shown and which inputs are received, the configuration device 18 transmits configuration data to the display/control unit 6 via the bus 15, which correspond to the position of attachment on the base unit 7 of the display and control device 2.

Details of the configuration process are explained below with reference to FIGS. 7A to E. Thereby considered is the use of a display and control device 2 according to the invention in a heart-lung machine (see FIG. 1) which, in addition to other units, comprises, for example, a sensor for monitoring the fill level, a blood reservoir and a detector for air bubbles in the arterial line, as well as temperature sensors for the blood entering the blood reservoir and the blood exiting the blood reservoir. These sensors and detectors, but also the other units and components of the HLM, are connected to the bus 15. The measured values of these sensors/detectors should be visualized using a display/control device 2 according to the invention, with it being defined as an example that the display always occurs in the area of the connector device 16a on the base unit 7 of the display and control device 2.

If a display/control unit 6 is now disposed at position 16a of the base unit 7 and a connection to the bus system 15 is established, the configuration device 18 transmits configuration data determining the display contents and input areas to the display/control unit 6.

In a first step, the configuration device transmits, for example, the configuration data:

(1) DispletPos="1"

Figure 7A:
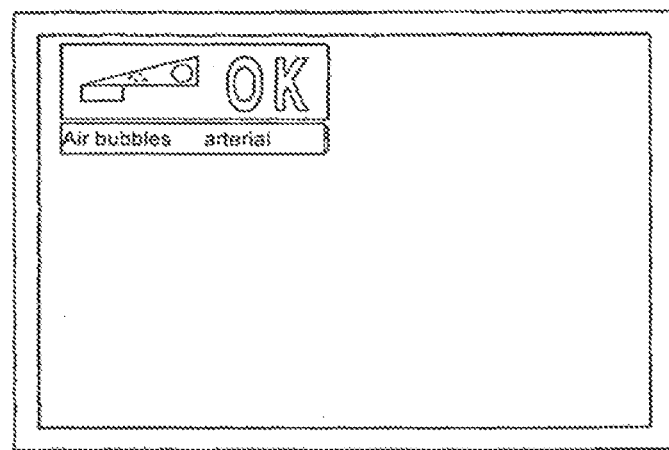
FIGS. 7A-7E show examples of display contents of a display/control unit according to the invention that are based on configuration data.

(2) Title Color="Blue" "Air bubbles arterial" to the display/control unit and causes the display/control unit 6 to display a blue title line with the text "Air bubbles arterial" in the topmost of three predefined lines in the left half of the display area 8, as is shown in FIG. 7A. The display area is a logical division of the otherwise advantageously continuous and undivided display 8 of the display/control unit 6. In a second step, the configuration device 18 transmits the configuration data (3) DispIcon1 Pic="Bubble Detector" to the display/control unit 6 and causes the display/control unit 6 to display a schematic image of an air bubble detector above the title line "Air bubbles arterial", as is also shown in FIG. 7A. In a third step, the configuration device 18 transmits the configuration data (4) ValueCan ="0000062" to the display/control unit 6, which cause the display/control unit 6 to receive values from the bus device having the identification 000062 via the electric bus 15. This identification is, for example, allocated to the air bubble detector of the HLM so that the display/control unit 6 is configured by the transmitted configuration data to receive sensor signals from the air bubble detector. In a fourth step, the configuration device 18 transmits the configuration data (5) ValIcon2 Pic="OK" Stat<"10"

(6) ValIcon2 Pic="Alarm" Stat>="10" to the display/control unit 6 and thus causes the display/control unit 6 to display the letters "OK" in the area above the title line "Air bubbles arterial" when the value obtained from the air bubble detector is less than 10. If the value is greater than or equal to 10, the configuration data contain the word "ALARM" which the display/control unit 6 displays instead of the letters "OK". In FIG. 7A the display "OK" is shown.

In order to define the display contents in the right half of the topmost line of the display/control unit 6, the configuration device 18 transmits the following configuration data (7) Displet="2"

(8) Title Color="Green" "Reservoir Level"

(9) ValueCan="000061"

(10) ValIcon1 Pic="FullRes" Stat>"75"

(11) ValIcon1 Pic="75% Res" Stat>"50"

(12) ValIcon1 Pic="50% Res" Stat>"25"

(13) ValIcon1 Pic="25% Res" Stat>"5"

(14) ValIcon1 Pic="0 g-Res" Stat>"0"

(15) ValIcon2 Pic="OK" Stat>"25"

Figure 7B:
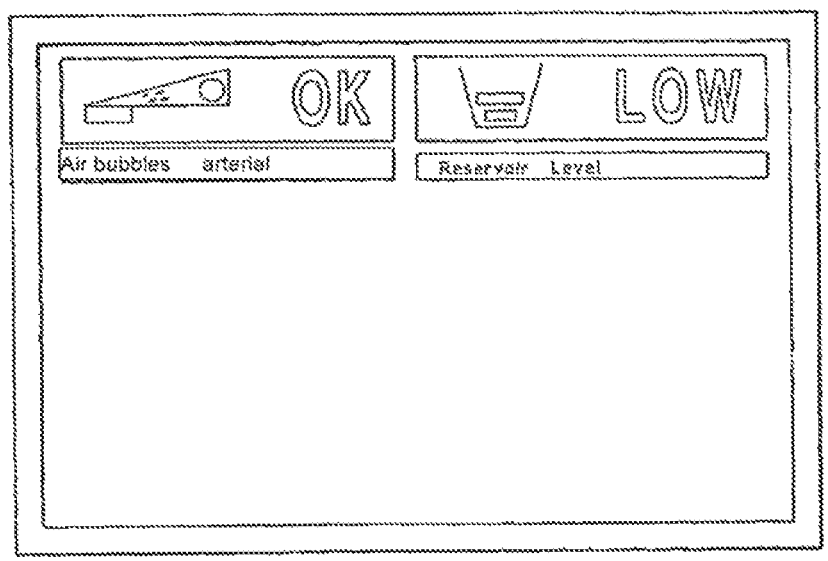

(16) ValIcon2 Pic"LOW" Stat<="25" to the display/control unit 6. The result of these configuration data is shown in FIG. 7B and arises as follows. In the configuration data, line (7) determines that the display segment in the right half of the topmost line of the display/control unit 6 is addressed. The configuration data in line (8) cause the display/control unit 6 to display a title line in green with the title "Reservoir level".

The configuration data in line (9) cause the display/control unit 6 to receive data from the unit connected to the electric bus with identification 000061. In the embodiment described herein, this is the fill level sensor which communicates the fill level of the blood reservoir of the HLM in question here as a value via the electric bus 15.

The configuration data in lines (10) to (14) cause the display/control unit 6 to display different graphics that reflect the fill level of the reservoir depending on the data received from the fill level sensor. The different graphics are thereby selected depending on steps 75%, 50%, 25% and 5%.

The configuration data in lines (15) and (16) cause the display/control unit 6 to furthermore display the letters "OK" in the top right area of the display if the value of the fill level sensor is greater than 25. The letters "OK" are replaced by the word "LOW" if the values of the fill level sensor are less than or equal to 25.

Figure 7C:
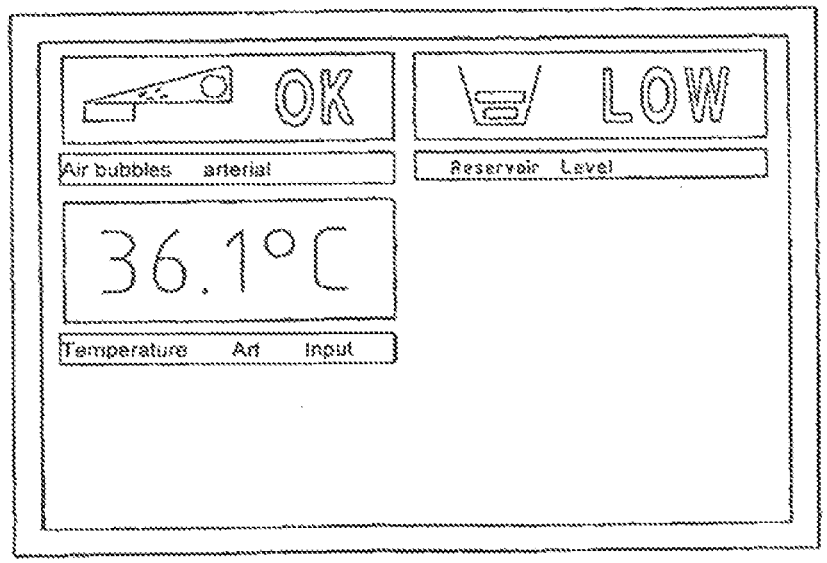

The following configuration data, whose display result is shown in FIG. 7C, cause the display/control unit 6 to display a title line in yellow with the wording "Temperature art. input" in the left half of the second line of display 8 and to furthermore show a temperature value with three digits and a decimal point and the unit "° C.", with the values to be shown originating from a temperature sensor with identification 000060.

(17) Displet="3"
(18) Title Color="Yellow" "Temperature art.input"
(19) ValueCan="000060"
(20) Value Fmt="%3d" Unit="° C."

Figure 7D:
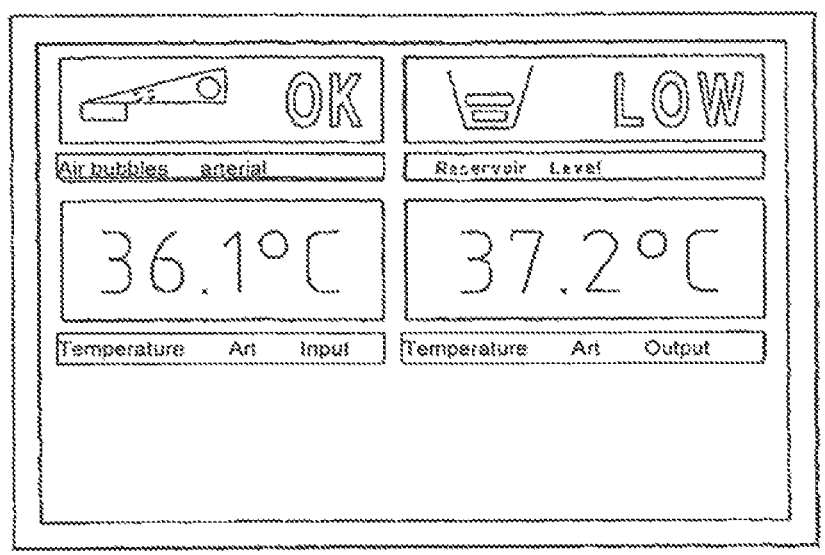

Accordingly, the following configuration data cause a display in the right half of the second line of display 8 of the display/control unit 6, as is shown in FIG. 7D, with the values to be shown here originating from a temperature sensor with identification 000059.

(21) Displet="4"
(22) Title Color="Yellow" "Temperature art.output"
(23) ValueCan="000059"
(24) Value Fmt="%3d" Unit="° C."

The configuration data described above furthermore cause the display/control unit 6 to define the area of the display above the title lines as an input areas. This means that if a user touches the surface of the display 8 of the display/control unit 6 in the area above one of the title lines, an input for the concerned sensor is received. If, for example, an alarm has been triggered because of too low a fill level in the blood reservoir (see FIG. 7B), the input area above the title line "Reservoir level" can be evaluated such that a touch in this area by the user is regarded as confirmation of the alarm.

Data which determine the input areas without establishing measured value displays can also be provided in the configuration data. In this way, switches, buttons or regulators can be shown which are operated by touching the touch-sensitive surface of the display/control unit 6.

Figure 7E:
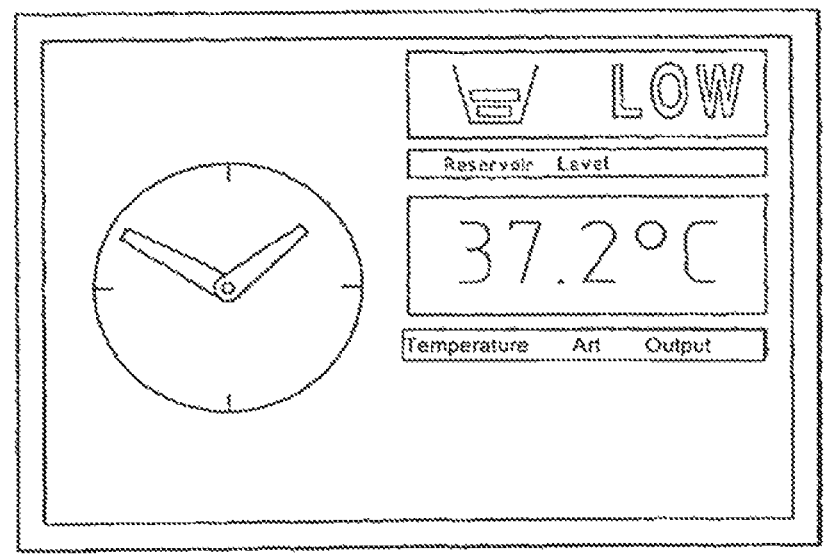

The various areas within the display of a display/control unit 6 can also be joined to form larger connected display areas. Thus, for example, FIG. 7E shows a configured display/control unit in which the three areas lying one above the other in the left half of the display 8 have been merged into one display area to create a display area which can accommodate the picture of an analogue clock. The configuration data transmitted by the configuration device of the display/control unit 6 for this display content have, for example, the following format:

(25) Displet="1,3,5"
(26) DisplIcon Pic="ClockAnalog"

The display contents to be shown by the display activation device 9 on the display 8 of the display/control unit 6 according to the invention are preferably stored in a memory of the display activation device 9. These are essentially digits and letters as well as graphic picture elements that represent measured values or operating states and also the units and components of the medical equipment. Storage of these data in the display activation device 9 means that the configuration device 18 need not transmit data for the depiction of the digits, letters and graphic images. This embodiment of a display and control device according to the invention is advantageous, however transmission of the data for the display contents from the configuration device can also be provided in control systems. In any case, it is advantageous if the display activation device 9 is able to receive additional data for display contents, to store these in a memory and to use these during operation for the picture of the display 8 of the display/control unit 6 according to the invention. This expands the usability of a display/control unit 6 according to the invention since if unknown display contents are produced, these can subsequently be transmitted by the configuration device 18 to the display/control unit 6. The display activation device 9 in this case is preferably able to inform the communication device 18 via the bus of which data are already stored in the display activation device 9 so that the configuration device 18 transmits only those data for the display contents which are not already present in the display activation unit 9.

The procedure described here for the structure, content and result of the configuration data as well as the type of bus system is given as an example and does not restrict the principle of the display and control device according to the invention, which can also be realized with other configuration data and other bus systems.

In the described embodiment, the position at which a display/control unit 6 was connected to the base unit 7 and thus to the bus 15 determined the function allocated to the display/control unit. This variant is advantageous since values and control elements always occur at the same point on the control panel. Alternatively, it can be provided that configuration data are transmitted in sequence to the display/control elements so that the user can determine at which point of the control panel which function is provided.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A heart lung machine comprising:
a plurality of pumps;
a display and control device operably connected to the plurality of pumps, the display and control device including:
an electric bus including a plurality of connector devices;
a plurality of touch screen displays, each of the plurality of touch screen displays including a display activation device, an input evaluation device that evaluates inputs made via the touch screen display, and a bus communication device releasably connected to one of the plurality of connector devices on the electric bus; and a configuration device operably connected with the electric bus, the configuration device configured to provide configuration information to each of the plurality of touch screen displays;

wherein if one of the plurality of touch screen displays fails, it can be replaced by removing the failed touch screen display from the electric bus and installing a replacement touch screen display in the same position on the electric bus during operation of the heart lung machine.

2. The heart lung machine of claim 1, wherein the replacement touch screen display comprises a redundant touch screen display that is not connected to the electric bus until being used as the replacement touch screen.

3. The heart lung machine of claim 1, wherein the replacement touch screen display comprises one of the plurality of touch screen displays, the replacement touch screen display removable from its initial position and installable in its replacement position replacing the failed touch screen display.

4. The heart lung machine of claim 1, wherein the configuration device determines which information is displayed on each of the plurality of touch screen displays in the absence of any detected failure.

5. The heart lung machine of claim 4, wherein the order in which information is selected to be displayed on each of the plurality of touch screen displays corresponds to the order in which the touch screen displays are connected to the electric bus.

6. The heart lung machine of claim 1, wherein two or more adjacent of the plurality of touch screen displays can be visually combined in a single display.

7. The heart lung machine of claim 1, wherein at least some of the plurality of touch screen displays are identical.

8. The heart lung machine of claim 1, wherein at least some of the plurality of touch screen displays are configured such that data for display contents can be stored in the touch screen displays.

9. The heart lung machine of claim 1, wherein at least some of the plurality of touch screen displays are configured to accommodate data entry.

10. The heart lung machine of claim 1, wherein the display and control device is the only control element operably connected to the heart lung machine.

11. The heart lung machine of claim 1, wherein an on/off switch and the display and control device are the only control elements operably connected to the heart lung machine.

12. The heart lung machine of claim 1, further comprising a blood reservoir.

13. The heart lung machine of claim 1, further comprising a fill level sensor operably connected to the electric bus.

14. The heart lung machine of claim 1, further comprising a blood temperature sensor operably connected to the electric bus.

15. A method of operating a heart lung machine including a plurality of pumps and a display and control device operably connected to the plurality of pumps, the display and control device comprising an electric bus and a plurality of touch screen displays connected to the electric bus, the method comprising:

operating the heart lung machine;

detecting a failure in one of the plurality of touch screen displays;

removing the failed touch screen display from the electric bus;

installing a replacement touch screen display on the electric bus in the position previously held by the failed touch screen display;

providing configuration information to the replacement touch screen display as soon as the replacement touch screen display is connected to the electric bus; and returning to normal operation of the heart lung machine.

16. The method of claim 15, wherein installing a replacement touch screen display comprises installing a touch screen display not previously connected to the electric bus.

17. The method of claim 15, wherein installing a replacement touch screen display further comprises removing a functioning touch screen display from the electric bus and using the functioning touch screen display as the replacement touch screen display.

* * * * *